(12) United States Patent
Donde et al.

(10) Patent No.: US 8,299,068 B2
(45) Date of Patent: Oct. 30, 2012

(54) THERAPEUTICALLY ACTIVE CYCLOPENTANES

(75) Inventors: Yariv Donde, Dana Point, CA (US); Jeremiah H. Nguyen, La Puente, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/011,082

(22) Filed: Jan. 21, 2011

(65) Prior Publication Data

US 2011/0190286 A1   Aug. 4, 2011

Related U.S. Application Data

(60) Provisional application No. 61/299,562, filed on Jan. 29, 2010.

(51) Int. Cl.
*A61K 31/5355* (2006.01)
*A61K 31/381* (2006.01)

(52) U.S. Cl. ............... 514/231.5; 514/448; 544/146; 549/71

(58) Field of Classification Search .................. None
See application file for complete search history.

(56) References Cited

U.S. PATENT DOCUMENTS

| | | | |
|---|---|---|---|
| 4,012,429 A | 3/1977 | Sakai et al. | |
| 4,166,452 A | 9/1979 | Generales, Jr. | |
| 4,256,108 A | 3/1981 | Theeuwes | |
| 4,265,874 A | 5/1981 | Bonsen et al. | |
| 5,698,598 A | 12/1997 | Woodward | |
| 5,877,211 A | 3/1999 | Woodward | |
| 6,262,293 B1 * | 7/2001 | Tani et al. | 560/18 |
| 7,091,231 B2 | 8/2006 | Donde et al. | |
| 7,427,685 B2 | 9/2008 | Donde et al. | |
| 7,585,895 B2 | 9/2009 | Donde et al. | |
| 7,960,378 B2 * | 6/2011 | Holoboski et al. | 514/231.5 |
| 2006/0205800 A1 | 9/2006 | Donde et al. | |
| 2007/0129552 A1 | 6/2007 | Donde et al. | |

FOREIGN PATENT DOCUMENTS

| | | |
|---|---|---|
| WO | WO 2006063179 | 6/2006 |
| WO | WO 2008/008718 | 1/2008 |
| WO | WO 2008073752 | 6/2008 |
| WO | WO 2008094958 | 8/2008 |
| WO | WO 2009/006370 | * 1/2009 |

OTHER PUBLICATIONS

Byrn et al. Solid-State Chemistry of Drugs, 2$^{nd}$ ed. Chapter 11, "Hydrates and Solvates," p. 233-247.*
U.S. Appl. No. 11/553,143, filed Jun. 7, 2007, Donde et al.
U.S. Appl. No. 12/265,062, filed Nov. 5, 2008, Donde et al.
"Prodrugs and Drug Delivery Systems," which is a chapter in Richard B. Silverman, Organic Chemistry of Drug Design and Drug Action, 2d Ed., Elsevier Academic Press: Amsterdam, 2004, pp. 496-557.
Remington's Pharmaceutical Sciences, Mack Publishing Company, Easton, Pa., 16th Edition, 1980.
Tani K et al: "Development of a highly selective EP2-receptor agonist. Part 2: identification of 16-hydroxy-17,17-trimethylen 9-beta-chloro PGF derivatives", Bioorganic & Medicinal Chemistry, vol. 10, No. 4, Jan. 1, 2002, pp. 1107-1114.

* cited by examiner

*Primary Examiner* — Joseph K. McKane
*Assistant Examiner* — Alicia L Otton
(74) *Attorney, Agent, or Firm* — Kevin J. Forrestal

(57) ABSTRACT

Disclosed herein are compounds having a formula:

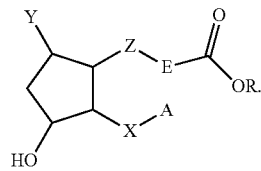

Therapeutic methods, medicaments, and compositions related thereto are also disclosed.

19 Claims, No Drawings

THERAPEUTICALLY ACTIVE CYCLOPENTANES

RELATED APPLICATION

This application claims the benefit of U.S. Provisional Application Ser. No. 61/299,562, filed Jan. 29, 2010, the disclosure of which is hereby incorporated in its entirety herein by reference.

FIELD OF THE INVENTION

The present invention relates generally to compounds and methods for treating ocular disorders. The invention relates specifically to the use of certain well-defined cyclopentanes for the treatment of ocular hypertension and glaucoma.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage. Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

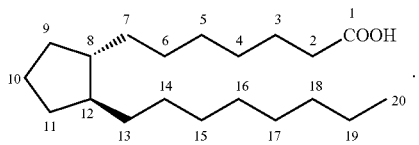

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

SUMMARY OF THE INVENTION

The invention provides well-defined cyclopentanes for treating glaucoma and ocular hypertension. In one embodiment of the invention, there are provided compounds having the structure:

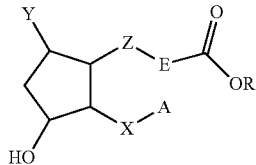

wherein:
Y is —Cl, —F, —Br, —CN, or —$CF_3$;
X $C_0$-$C_{14}$ optionally substituted alkylene, optionally substituted alkenylene, or optionally substituted alkynylene;
Z is optionally substituted methylene or $C_2$-$C_{14}$ optionally substituted alkylene, optionally substituted alkenylene, or optionally substituted alkynylene;
E is interarylene or interheteroarylene;
R is H, $C_{1-6}$ alkyl, phenyl, —$CH_2CH_2OH$, or —$CH_2CH_2$—$N(R^1)_2$ wherein $R^1$ is $C_1$ to $C_6$ alkyl, or each $R^1$ taken together with the nitrogen atom forms a ring optionally containing an additional heteroatom; and
A is optionally substituted cycloalkyl or optionally substituted cycloalkenyl;
or pharmaceutically acceptable salts, hydrates, solvates, and crystal forms, isomers, tautomers, enantiomers, and diastereomers thereof.

In another embodiment of the invention, there are provided compositions including at least one compound of the invention, wherein the composition is a liquid which is ophthalmically acceptable.

In another embodiment of the invention there are provided methods for treating glaucoma or ocular hypertension. Such methods can be performed, for example, by administering to a subject in need thereof a compound of the invention.

In still another embodiment of the invention, there are provided kits including at least one composition of the invention, a container, and instructions for administration of the composition to a subject in need thereof for the treatment of glaucoma or ocular hypertension.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning Standard techniques may be used for chemical syntheses, chemical analyses, and formulation.

As used herein, "alkyl" refers to straight or branched chain hydrocarbyl groups having from 1 up to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, lower alkylamino, lower alkyldiamino, amido, azido, —C(O)H, —C(O)$R_D$, —CH$_2$OR$_7$, —C(O)—, —C(O)—, —S—, —S(O)$_2$, —OC(O)—O—, wherein $R_7$ is H or lower alkyl, acyl, oxyacyl, carboxyl, carbamate, sulfonyl, sulfonamide, sulfuryl, and the like. As used herein, "lower alkyl" refers to alkyl moieties having from 1 to about 6 carbon atoms.

As used herein, the term "alkylene" refers to a divalent alkyl moiety, meaning the alkylene moiety is attached to the rest of the molecule at both ends of the alkyl unit.

As used herein, "alkenyl" refers to straight or branched chain hydrocarbyl groups having at least one carbon-carbon double bond, and having in the range of about 2 up to about 100 carbon atoms, and "substituted alkenyl" refers to alkenyl groups further bearing one or more substituents as set forth above. As used herein, "lower alkenyl" refers to alkenyl moieties having from 2 to about 6 carbon atoms.

As used herein, the term "alkenylene" refers to a divalent alkenyl moiety, meaning the alkenylene moiety is attached to the rest of the molecule at two positions.

As used herein, "alkynyl" refers to straight or branched chain hydrocarbyl groups having at least one carbon-carbon triple bond, and having in the range of about 2 up to about 100 carbon atoms, and "substituted alkynyl" refers to alkynyl groups further bearing one or more substituents as set forth above. As used herein, "lower alkynyl" refers to alkynyl moieties having from 2 to about 6 carbon atoms.

As used herein, "cycloalkyl" refers to cyclic (i.e., ring-containing) alkyl moieties typically containing in the range of about 3 up to about 8 carbon atoms, and "substituted cycloalkyl" refers to cycloalkyl groups further bearing one or more substituents as set forth above. "Cycloalkyl" also refers to bicyclic moieties, such as norbornyl, and the like.

As used herein, "cycloalkenyl" refers to cyclic (i.e., ring-containing) alkenyl moieties typically containing in the range of about 3 up to about 8 carbon atoms, and "substituted cycloalkenyl" refers to cycloalkenyl groups further bearing one or more substituents as set forth above. "Cycloalkenyl" also refers to bicyclic moieties, such as norbornenyl, and the like.

As used herein, "aryl" refers to aromatic groups having in the range of 5 up to 14 carbon atoms and "substituted aryl" refers to aryl groups further bearing one or more substituents as set forth above.

As used herein, "heteroaryl" refers to aromatic moieties containing one or more heteroatoms (e.g., N, O, S, or the like) as part of the ring structure and having in the range of 5 up to 14 total atoms in the ring structure (i.e., carbon atoms and heteroatoms). "Substituted heterocyclic" refers to heterocyclic groups further bearing one or more substituents as set forth above.

As used herein "interarylene" refers to an aryl ring or ring system or a heteroaryl ring or ring system which connects two other parts of a molecule, i.e. the two parts are bonded to the ring in two distinct ring positions. Interarylene or interheteroarylene may be substituted or unsubstituted. Unsubstituted interarylene or interheteroarylene has no substituents other than the two parts of the molecule it connects. Substituted interarylene or interheteroarylene has substituents in addition to the two parts of the molecule it connects.

As used herein, "heterocyclic" refers to non-aromatic cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As used herein, "halogen" or "halide" refers to fluoride, chloride, bromide or iodide. "Fluoride, chloride, bromide or iodide" may also be referred to as "fluoro, chloro, bromo, or iodo".

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The invention provides well-defined cyclopentanes having the structure:

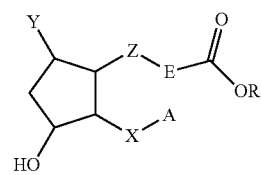

wherein:

Y is —Cl, —F, —Br, —CN, or —CF$_3$;

X is $C_0$-$C_{14}$ optionally substituted alkylene, optionally substituted alkenylene, or optionally substituted alkynylene;

Z is optionally substituted methylene or $C_2$-$C_{14}$ optionally substituted alkylene, optionally substituted alkenylene, or optionally substituted alkynylene;

E is interarylene or interheteroarylene;

R is H, $C_{1-6}$ alkyl, phenyl, —CH$_2$CH$_2$OH, or —CH$_2$CH$_2$—N(R$_1$)$_2$ wherein R$^1$ is $C_1$ to $C_6$ alkyl, or each R$^1$ taken together with the nitrogen atom forms a ring optionally containing an additional heteroatom; and A is optionally substituted cycloalkyl or optionally substituted cycloalkenyl;

or pharmaceutically acceptable salts, hydrates, solvates, and crystal forms, isomers, tautomers, enantiomers, and diastereomers thereof.

In some embodiments of the invention, Y is —Cl, —F, —CN, or —CF$_3$. In one embodiment, Y is —Cl. In another embodiment Y is —F. In another embodiment Y is —CN. In another embodiment Y is —Br. In another embodiment Y is —CF$_3$.

In some embodiments of the invention, X and Z are each independently $C_2$-$C_6$ alkylene, alkenylene, or alkynylene. In certain embodiments, X is $C_2$ alkylene, alkenylene, or alkynylene. In certain embodiments, Z is $C_3$ alkylene, alkenylene, or alkynylene.

In some embodiments of the invention the interarylene or interheteroarylene is substituted or unsubstituted interphenylene, interthiophenylene, interfurylene, interpyridinylene, interoxazolylene, or interthiazolene. In certain embodiments of the invention, the interarylene is interthiophenylene. In other embodiments the interheteroarylene is furylene and interthiazolene.

In other embodiments of the invention A is cycloalkyl. In certain embodiments A is cyclopentyl or cyclohexyl.

The compounds of the invention may contain a wide a variety of substituents. When invention compounds bear substituents, the substituents are typically selected from alkyl, alkenyl, alkynyl, hydroxy, alkoxy, heterocyclic, aryl, heteroaryl, aryloxy, halogen, haloalkyl, cyano, nitro, amino, lower alkylamino, lower dialkylamino, amido, azido, acyl (—C(O)R$_6$), alkoxymethyl, mercapto (—S—R$_6$), sulfoxy (—S(O)—R$_6$), sulfonyl (—S(O)$_2$—R$_6$), sulfonamide (—S(O)$_2$N(R$_6$)$_2$), carbonate (—OC(O)—O—R$_6$), oxyacyl (—OC(O)—R$_6$), carboxyl (—C(O)OH), ester (—C(O)OR$_6$), carbamate (—OC(O)—N(R$_6$)$_2$), wherein R$_6$ is H or lower alkyl, lower alkenyl, lower alkynyl, aryl, heteroaryl, heterocycle, and the like.

In certain embodiments of the invention, Z, X, and A bear hydroxy substituents.

Exemplary compounds contemplated for use in the practice of the invention include, but are not limited to, 5-(3-((1R,2R,3R,5R)-5-chloro-3-hydroxy-2-(2-(1 pentylcyclohexyl)ethyl)cyclopentyl)propyl)thiophene-2-carboxylic acid;

methyl 5-(3-((1R,2R,3R,5R)-5-chloro-3-hydroxy-2-(2-(1-pentylcyclohexyl)ethyl)cyclopentyl)propyl)thiophene-2-carboxylate;

5-(3-((1R,2R,3R,5R)-5-chloro-2-(E)-2-cyclopentylvinyl)-3-hydroxycyclopentyl)propyl)thiophene-2-carboxylic acid;

methyl 5-(3-((1R,2R,3R,5R)-5-chloro-2-(E)-2-cyclopentylvinyl)-3-hydroxycyclopentyl)propyl)thiophene-2-carboxylate;

methyl 5-(3-((1R,2R,3R,5R)-5-chloro-2-(2-cyclopentylethyl)-3-hydroxycyclopentyl)propyl)thiophene-2-carboxylate;

5-(3-((1R,2R,3R,5R)-5-chloro-2-(2-cyclopentylethyl)-3-hydroxycyclopentyl)propyl)thiophene-2-carboxylic acid;

5-(3-((1R,2R,3R,5R)-5-chloro-2-(2-cyclohexylethyl)-3-hydroxycyclopentyl)propyl)thiophene-2-carboxylic acid;

methyl 5-(3-((1R,2R,3R,5R)-5-chloro-2-(2-cyclohexylethyl)-3-hydroxycyclopentyl)propyl)thiophene-2-carboxylate;

methyl 5-(3-((1R,2R,3R,5R)-5-chloro-2-(E)-2-cyclohexylvinyl)-3-hydroxycyclopentyl)propyl)thiophene-2-carboxylate; or 5-(3-((1R,2R,3R,5R)-5-chloro-2-(E)-2-cyclohexylvinyl)-3-hydroxycyclopentyl)propyl)thiophene-2-carboxylic acid.

In other embodiments of the invention, esters of invention compounds are contemplated for use. As such, R consists of: 1) $C_{1-6}$ alkyl or phenyl, and 2) from 0 to 2 —OH moieties. In other words, examples of R include:

—CH$_3$, —C$_2$H$_5$, —C$_3$H$_7$, —C$_4$H$_9$, C$_5$H$_{11}$, —C$_6$H$_{13}$, cyclic —C$_3$H$_6$, cyclic —C$_4$H$_8$, cyclic —C$_5$H$_{10}$, or cyclic —C$_6$H$_{12}$, wherein "cyclic" indicates the presence of a ring;

—CH$_2$—OH, —C$_2$H$_4$—OH, —C$_3$H$_6$—OH, —C$_4$H$_8$—OH, C$_5$H$_{10}$—OH, —C$_6$H$_{12}$—OH, cyclic —C$_3$H$_5$OH, cyclic —C$_4$H$_7$—OH, cyclic —C$_5$H$_9$—OH, or cyclic —C$_6$H$_{11}$—OH, wherein the —OH may be in any position on the hydrocarbyl moiety;

—C$_2$H$_3$—(OH)$_2$, —C$_3$H$_5$—(OH)$_2$, —C$_4$H$_7$—(OH)$_2$, —C$_5$H$_9$—(OH)$_2$, or —C$_6$H$_{11}$—(OH)$_2$, cyclic —C$_3$H$_4$—(OH)$_2$, cyclic —C$_4$H$_6$—(OH)$_2$, cyclic —C$_5$H$_8$—(OH)$_2$, or cyclic —C$_6$H$_{10}$—(OH)$_2$, wherein —(OH)$_2$ represents 2 distinct —OH moieties, and each —OH may be in any position on the hydrocarbyl moiety; or

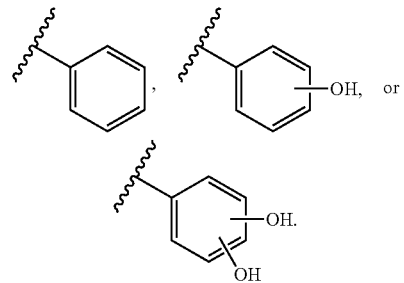

In other embodiments, ethyldialkylamino esters are contemplated for use in the practice of the invention. In this embodiment —CH$_2$CH$_2$—N(R$^1$)$_2$ wherein R$^1$ is $C_1$ to $C_6$ alkyl, or each R$^1$ taken together with the nitrogen atom forms a ring optionally containing an additional heteroatom.

Exemplary esters include, but are not limited to, the following compounds:

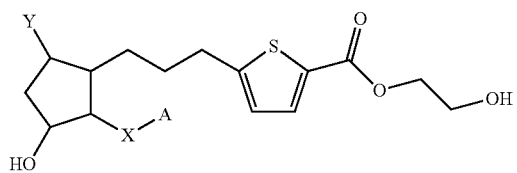

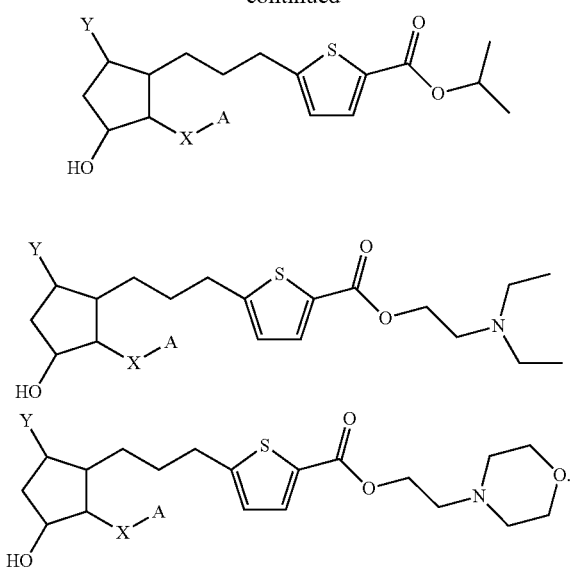

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring. Salts can form from or incorporate one or more deprotonated acidic groups (e.g. carboxylic acids), one or more protonated basic groups (e.g. amines), or both (e.g. zwitterions).

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted.

Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject. In particular, alkyl esters having such as methyl, ethyl, isopropyl, and the like are contemplated. Also contemplated are prodrugs containing a polar group such as hydroxyl or morpholine. Examples of such prodrugs include compounds containing the moieties —$CO_2(CH_2)_2OH$, and the like.

The compounds of the invention are useful for reducing intraocular pressure. Reduction of intraocular pressure has been shown to delay or prevent the onset of primary open angle glaucoma, and to delay or prevent further vision loss in patients with primary open angle glaucoma. Thus, these compounds are also useful for treating glaucoma. Different types of suitable dosage forms and medicaments are well known in the art, and can be readily adapted for delivery of the compounds disclosed herein. For example, the compound could be dissolved or suspended in an aqueous solution or emulsion that is buffered to an appropriate pH, and administered topically to an eye of a mammal (see U.S. Pat. No. 7,091,231).

For the purposes of this disclosure, "treat," "treating," or "treatment" refer to the use of a compound, composition, therapeutically active agent, or drug in the diagnosis, cure, mitigation, treatment, or prevention of disease or other undesirable condition.

Unless otherwise indicated, reference to a compound should be construed broadly to include pharmaceutically acceptable salts, prodrugs, tautomers, alternate solid forms, non-covalent complexes, and combinations thereof, of a chemical entity of a depicted structure or chemical name.

Tautomers are isomers that are in rapid equilibrium with one another. For example, tautomers may be related by transfer of a proton, hydrogen atom, or hydride ion. Unless stereochemistry is explicitly and unambiguously depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The following examples are intended only to illustrate the invention and should in no way be construed as limiting the invention.

EXAMPLES

Synthetic Methods

While there are many ways to prepare the compounds disclosed herein, useful compounds may be obtained by using or adapting the following exemplary procedures.

Scheme 1

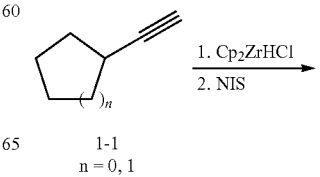

1-1
n = 0, 1

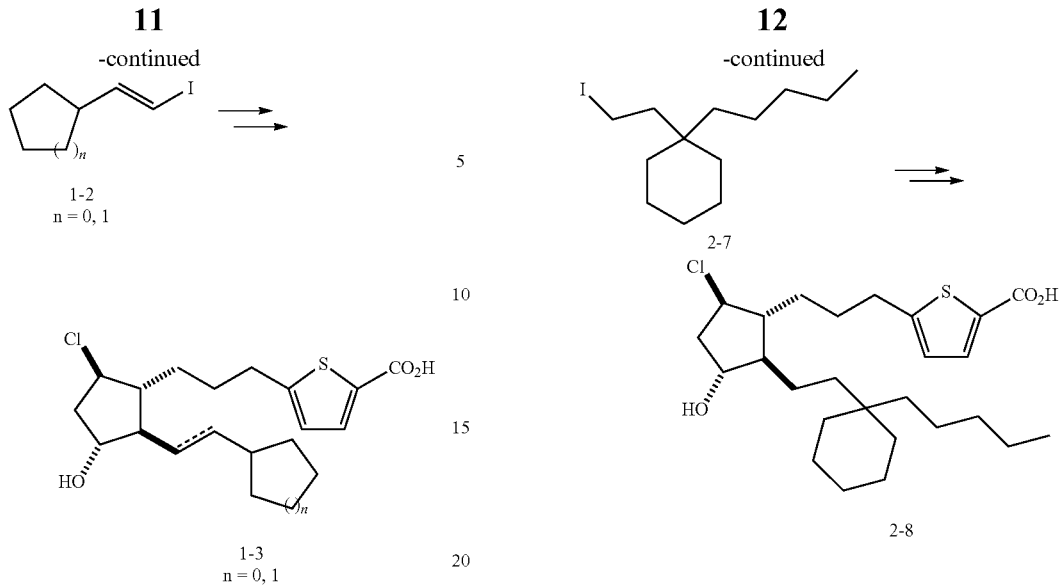

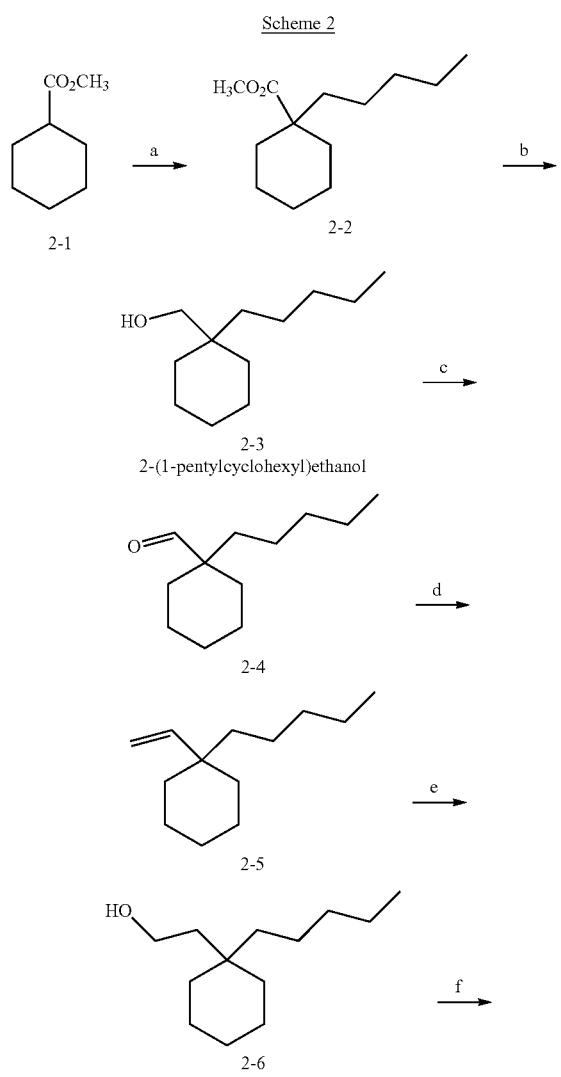

Conditions: (a) LDA; n-pentyliodide, HMPA; (b) LiAlH$_4$; (c) Swern [O]; (d) Ph$_3$PCH$_3$Br, tert-BuOK; (e) 9-BBN; H$_2$O$_2$; NaOH, H$_2$O; (f) Ph$_3$P, I$_2$, imidazole, CH$_2$Cl$_2$.

Representative procedure: (E)-(2-iodovinyl)cyclopentane (1-2, n=1). Cp$_2$ZrHCl (1.805 g, 7.00 mmol) was added to a solution of alkyne 1-1 (n=1,497 mg, 4.60 mmol) in CH$_2$Cl$_2$ (19 mL). The reaction was stirred for 45 min. and N-iodosuccinimide (NIS, 1.552 g, 6.90 mmol) was added. After 2 h, saturated NaHCO$_3$ solution (20 mL) was added and the resulting mixture was extracted with CH$_2$Cl$_2$ (3×50 mL). The combined CH$_2$Cl$_2$ solution was washed with brine and then was dried (Na$_2$SO$_4$), filtered and evaporated. The residue was purified by flash chromatography using a Combiflash system by Teledyne Isco (40 g silica gel, 0→100% ethyl acetate/ hexanes) which gave the title compound (978 mg, 90%). The intermediate iodides were converted to the final compounds (1-3) by a sequence similar to that described in U.S. patent application Ser. No. 12/265,062.

Methyl 1-pentylcyclohexanecarboxylate (2-2). A solution of ester 2-1 (2.053 g, 14.4 mmol) in THF (22 mL) was added, by cannula, to a −78° C. solution of LDA (8 mL, 16 mmol, 2 M in heptanes/THF/ethyl benzene from Aldrich), rinsing with 1 mL THF. After 30 min., a solution of n-pentyliodide (3.147 g, 15.9 mmol) in HMPA (2.6 mL) was added. The resulting solution was stirred for 10 min. at −78° C. and then was allowed to warm to room temperature. After 1 h, 100 mL H$_2$O was added. The resulting mixture was extracted with ethyl acetate and the ethyl acetate solution was washed with H$_2$O (3×100 mL) and brine and then was dried (Na$_2$SO$_4$), filtered and evaporated. The residue was purified by flash chromatography using a Combiflash system by Teledyne Isco (120 g silica gel, 0→25% ethyl acetate/hexanes) which gave the title compound (1.773 g, 12.5 mmol, 87%).

(1-Pentylcyclohexyl)methanol (2-3). LiAlH$_4$ (15 mL, 30 mmol, 2 M/THF) was added drop wise to a solution of 2-2 (1.773 g, 12.5 mmol) in ether (9 mL) at a rate to maintain a gentle reflux. The mixture was stirred further for 15 min. and then was cooled to 0° C. H$_2$O (1 mL) was added followed by 3 M NaOH (1.2 mL) and more H$_2$O (3 mL). The resulting mixture was allowed to warm to room temperature and after 1 h of stirring, 50 mL saturated NH$_4$Cl solution was added. The mixture was extracted with dichloromethane (3×30 mL) and the combined dichloromethane solution was washed with brine and then was dried (Na$_2$SO$_4$), filtered and evaporated. The residue was purified by flash chromatography using a combiflash system by Teledyne Isco (80 g silica gel, 0→100% ethyl acetate/hexanes) which gave the title compound (968 mg, 5.3 mmol, 42%).

1-Pentylcyclohexanecarbaldehyde (2-4). DMSO (930 L) was added to a −78° C. solution of oxalyl chloride (3.2 mL, 2 M/toluene) in CH$_2$Cl$_2$ (44 mL). After 15 min., a solution of alcohol 2-3 (968 mg, 5.3 mmol) in 14 mL CH$_2$Cl$_2$ was added by cannula, rinsing with 2 mL CH$_2$Cl$_2$. The reaction was stirred for 15 min. and Et$_3$N (5.9 mL) was added. The reaction was allowed to warm to 0° C. and after 2 h, 100 mL saturated NaHCO$_3$ solution was added. The resulting mixture was extracted with CH$_2$Cl$_2$ (3×) and the combined CH$_2$Cl$_2$ solution was washed with H$_2$O and brine and then was dried (Na$_2$SO$_4$), filtered and evaporated to give the title compound.

1-Pentyl-1-vinylcyclohexane (2-5). Tert-BuOK (2.2 mL, 2.2 mmol, 1 M/THF) was added to a solution of Ph$_3$PCH$_3$Br (1.42 mmol) in THF (7.2 mL). After 1 h, a solution of aldehyde 2-4 (130 mg, 0.71 mmol) in THF (2 mL) was added by cannula, rinsing with 1 mL THF. The reaction was stirred at room temperature for 2 h and was then quenched by addition of 10 mL saturated NH$_4$Cl solution. The resulting mixture was extracted with ethyl acetate (3×20 mL) and the combined ethyl acetate solution was dried (Na$_2$SO$_4$), filtered and evaporated. The residue was purified by flash chromatography using a Combiflash system by Teledyne Isco (4 g silica gel, 0→50% ethyl acetate/hexanes) which gave the title compound (62 mg, 0.34 mmol, 48%).

2-(1-Pentylcyclohexyl)ethanol (2-6). A solution of 2-5 (90 mg, 0.50 mmol) in THF (3.4 mL) was added to a solution of 9-BBN dimer (206 mg, 0.84 mmol) in THF (3 mL). The reaction was placed in a 60° C. oil bath and after 2.5 h, a solution of H$_2$O$_2$ (35%, 1.4 mL)/NaOH (0.5 M, 1.4 mL)/H$_2$O (0.35 mL) was added. The reaction was heated to reflux for 1 h and then allowed to cool to room temperature. H$_2$O (20 mL) was added and the mixture was extracted with ethyl acetate (3×25 mL). The combined ethyl acetate solution was washed with brine and then was dried (Na$_2$SO$_4$), filtered and evaporated. The residue was purified by flash chromatography using a Combiflash system by Teledyne Isco (4 g silica gel, 0→30% ethyl acetate/hexanes) which gave the title compound (70 mg, 71%).

1-(2-iodoethyl)-1-pentylcyclohexane (2-7). The procedure used to prepare the title compound was described in U.S. Pat. No. 7,091,231 B2.

5-(3-((1R,2R,3R,5R)-5-chloro-3-hydroxy-2-(2-(1-pentylcyclohexyl)ethyl)cyclopentyl)propyl)thiophene-2-carboxylic acid (2-8). The title compound was prepared using a sequence described in U.S. patent application Ser. No. 12/265,062.

In Vivo Example

U.S. Pat. No. 7,091,231, incorporated by reference herein, describes the methods used to obtain the in vivo test results presented in Table 1.

TABLE 1

| ENTRY | STRUCTURE | Conc. (g/100 mL) | DOG | | MONKEY |
|---|---|---|---|---|---|
| | | | Max. IOP (%) | Max. hyperemia | Max. IOP (%) |
| 1 | [structure: cyclopentane with Cl, OH, propyl-thiophene-CO$_2$H, and 2-(1-cyclohexyl)ethyl substituents] | 0.005% | 40 | 2.0 | 47 |

In Vitro Examples

U.S. Pat. No. 7,427,685 incorporated by reference herein, describes the methods used to obtain the in vitro data in Table 2 below.

| Entry | STRUCTURE | cAMP EC50 (nM) | Ki (nM) | EP2 Ca2+ EC50 (nM) | EP4 Ca2+ EC50 (nM) | Ki (nM) | OTHER RECEPTORS Ca2+ EC50 (nM) |
|---|---|---|---|---|---|---|---|
| 1 | [structure: cyclopentane with Cl, OH, propyl-thiophene-CO$_2$H, and 2-(1-cyclopentyl)ethyl substituents] | 0.6 | 9 | 4 | 3070 | 2617 | DP(259) NA: EP1, EP3, FP, IP, TP |

-continued

| Entry | STRUCTURE | cAMP EC50 (nM) | Ki (nM) | EP2 Ca2+ EC50 (nM) | Ca2+ EC50 (nM) | EP4 Ki (nM) | OTHER RECEPTORS Ca2+ EC50 (nM) |
|---|---|---|---|---|---|---|---|
| 2 | (structure) | 0.9 | 10 | 3 | 1349 | 2737 | DP(191), NA: EP1, EP3, FP, IP, TP |
| 3 | (structure) | 0.2 | 0.8 | 12 | 6639 | 2154 | DP(548), EP3(9052) NA: EP1, FP, IP, TP |
| 4 | (structure) | 0.5 | 4 | 7 | 3,322 | 2709 | DP(2162), EP3(5221) NA: EP1, FP, IP, TP |
| 5 | (structure) | 152 | 1038 | 2412 | 9330 | 5059 | NA: DP, EP1, EP3, FP, IP, |

While this invention has been described with respect to these specific examples, it is understood that other modifications and variations are possible without departing from the spirit of the invention.

What is claimed is:

1. A compound of a formula:

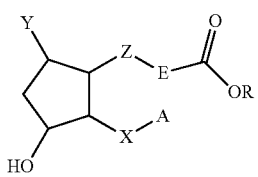

wherein:
Y is —Cl, —F, —Br, —CN, or —CF$_3$;
X is C$_0$-C$_{14}$ alkylene, alkenylene, or alkynylene;
Z is optionally substituted methylene or C$_2$-C$_{14}$ optionally substituted alkylene, optionally substituted alkenylene, or optionally substituted alkynylene;
E is interarylene or interheteroarylene;
R is H, C$_{1-6}$ alkyl, phenyl, —CH$_2$CH$_2$OH, or —CH$_2$CH$_2$—N(R$^1$)$_2$ wherein R$^1$ is C$_1$ to C$_6$ alkyl, or each R$^1$ taken together with the nitrogen atom forms a ring optionally containing an additional heteroatom; and
A is unsubstituted cycloalkyl;
or pharmaceutically acceptable salts, tautomers, enantiomers, and diastereomers thereof.

2. The compound of claim 1 wherein X is C$_2$-C$_6$ alkylene, alkenylene, or alkynylene.

3. The compound of claim 1 wherein X is C$_2$ alkylene, alkenylene, or alkynylene.

4. The compound of claim 3 wherein the interarylene or interheteroarylene is substituted or unsubstituted interthiophenylene.

5. The compound of claim 1 wherein Z is C$_2$-C$_6$ alkylene, alkenylene, or alkynylene.

6. The compound of claim 1 wherein Z is C$_3$ alkylene, alkenylene, or alkynylene.

7. The compound of claim 1 wherein A is cyclopentyl or cyclohexyl.

8. The compound of claim 1 wherein the interarylene or interheteroarylene is substituted or unsubstituted interphenylene, interthiophenylene, interfurylene, interpyridinylene, interoxazolylene, or interthiazolene.

9. The compound of claim 8 wherein the interarylene is interthiophenylene.

10. The compound of claim 1 selected from:

methyl 5-(3-((1R,2R,3R,5R)-5-chloro-3-hydroxy-2-(2-(1-pentylcyclohexyl)ethyl)cyclopentyl)propyl)thiophene-2-carboxylate;

5-(3-((1R,2R,3R,5R)-5-chloro-2-(E)-2-cyclopentylvinyl)-3-hydroxycyclopentyl)propyl)thiophene-2-carboxylic acid;

methyl 5-(3-((1R,2R,3R,5R)-5-chloro-2-(E)-2-cyclopentylvinyl)-3-hydroxycyclopentyl)propyl)thiophene-2-carboxylate;

methyl 5-(3-((1R,2R,3R,5R)-5-chloro-2-(2-cyclopentylethyl)-3-hydroxycyclopentyl)-propyl)thiophene-2-carboxylate;

5-(3-((1R,2R,3R,5R)-5-chloro-2-(2-cyclopentylethyl)-3-hydroxycyclopentyl)-propyl)thiophene-2-carboxylic acid; 5-(3-((1R,2R,3R,5R)-5-chloro-2-(2-cyclohexylethyl)-3-hydroxycyclopentyl)propyl)thiophene-2-carboxylic acid;

methyl 5-(3-((1R,2R,3R,5R)-5-chloro-2-(2-cyclohexylethyl)-3-hydroxycyclopentyl)propyl)thiophene-2-carboxylate;

methyl 5-(3-((1R,2R,3R,5R)-5-chloro-2-(E)-2-cyclohexylvinyl)-3-hydroxycyclopentyl)propyl)thiophene-2-carboxylate; or 5-(3-((1R,2R,3R,5R)-5-chloro-2-(E)-2-cyclohexylvinyl)-3-hydroxycyclopentyl)propyl)thiophene-2-carboxylic acid.

11. The compound of claim 1 of the structure:

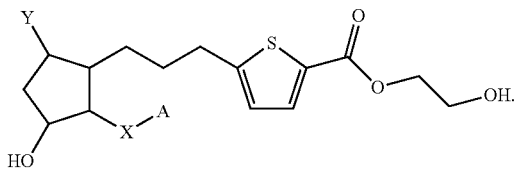

12. The compound of claim 1 of the structure:

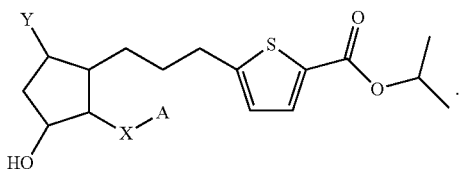

13. The compound of claim 1 of the structure:

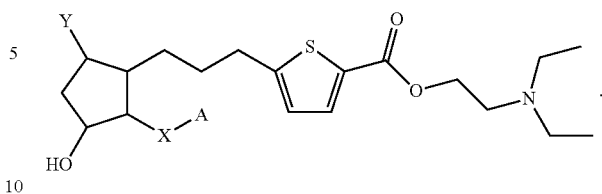

14. The compound of claim 1 of the structure:

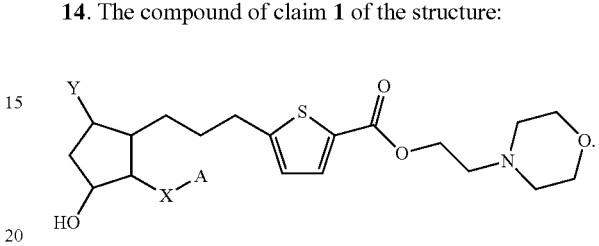

15. A compound of the structure

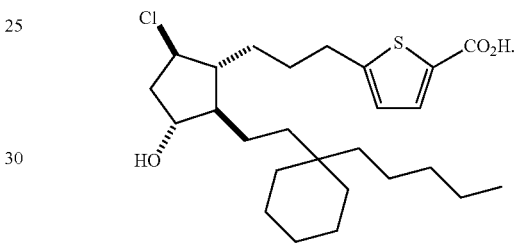

16. A composition comprising at least one compound according to claim 1, wherein the composition is a liquid which is ophthalmically acceptable.

17. A method of treating glaucoma or ocular hypertension comprising administering to a subject in need thereof a compound according to claim 1.

18. The method of claim 17 wherein the subject is human.

19. A kit comprising the composition of claim 16, a container, and instructions for administration of the composition to a subject in need thereof for the treatment of glaucoma or ocular hypertension.

* * * * *